United States Patent
Spoonhower et al.

(10) Patent No.: US 7,027,924 B2
(45) Date of Patent: Apr. 11, 2006

(54) DETECTING NATURAL GAS PIPELINE FAILURES

(75) Inventors: John P. Spoonhower, Webster, NY (US); Gustavo R. Paz-Pujalt, Rochester, NY (US); Janet M. Sherin, Walworth, NY (US); Martin G. Graen, Pittsford, NY (US); Steven V. Stearns, Pittsford, NY (US)

(73) Assignee: ITT Manufacturing Enterprises, Inc, Wilmington, DE (US)

( * ) Notice: Subject to any disclaimer, the term of this patent is extended or adjusted under 35 U.S.C. 154(b) by 30 days.

(21) Appl. No.: 10/285,244

(22) Filed: Oct. 31, 2002

(65) Prior Publication Data

US 2004/0088113 A1    May 6, 2004

(51) Int. Cl.
G01N 21/00    (2006.01)
G01M 3/08    (2006.01)

(52) U.S. Cl. .................. 702/8; 356/301; 250/253
(58) Field of Classification Search ............. 250/341.2, 250/253; 702/8, 5, 36, 40; 356/301
See application file for complete search history.

(56) References Cited

U.S. PATENT DOCUMENTS 3,662,171 A * 5/1972 Brengman et al. .......... 250/342
4,077,719 A * 3/1978 Barrett et al. ............... 356/301
4,507,558 A * 3/1985 Bonne ......................... 250/345
4,543,481 A * 9/1985 Zwick .................... 250/339.03
4,853,543 A * 8/1989 Ozdemir ..................... 250/372
5,212,099 A * 5/1993 Marcus ....................... 436/172
5,309,522 A * 5/1994 Dye ............................ 382/154
5,329,353 A * 7/1994 Ichimura et al. ........... 356/328
5,481,476 A 1/1996 Windig
5,822,058 A * 10/1998 Adler-Golden et al. ..... 356/303
6,389,881 B1 * 5/2002 Yang et al. .............. 73/40.5 A
6,422,508 B1 * 7/2002 Barnes ...................... 244/3.16
6,509,566 B1 * 1/2003 Wamsley et al. ........ 250/338.5
6,531,701 B1 * 3/2003 Chou et al. ............ 250/339.08

FOREIGN PATENT DOCUMENTS

EP    1 193 470 A2    3/2002
WO   WO 97/20167    6/1997
WO   WO 02/27297 A1    4/2002

* cited by examiner

Primary Examiner—Marc S. Hoff
Assistant Examiner—Paul Kim
(74) Attorney, Agent, or Firm—RatnerPrestia

(57) ABSTRACT

A method for detecting failures in a natural gas returning radiation from the pipeline; determining that there is a failure in the pipeline when the spectral or thermal signature indicates that there is a plume of escaping natural gas from the pipeline emitted from a failure; and indicating to a customer that a failure in the pipeline has been detected at a predetermined coordinate position.

14 Claims, 6 Drawing Sheets

DETECTING NATURAL GAS PIPELINE FAILURES

The present invention relates to remotely detecting natural gas pipeline failures.

BACKGROUND OF THE INVENTION

The surveillance of ground topography is well known in the art. It is frequently the case that an aircraft or a satellite includes an image capture device such as a charge coupled device (CCD). In ground surveillance it is highly desirable to detect whether there has been a material failure in a man-made object such as a road, a pipeline, an electrical grid, or other man-made structures of practical interest. When detected, a determination is made if remedial action must be taken. Often times a visual inspection of ground topography is provided by a land-based crew that traverses an area by vehicle or foot, to determine if there is a material failure. Airborne photographic systems can also be used for capturing images of adjacent areas. These images are then reviewed to determine if there is a material failure.

In detecting failures in gas pipelines there is a particular problem as the pipeline is typically buried beneath ground level. In such cases it is difficult to make direct visual assessment of the failures in pipelines. The fact remains that when failures occur and they are manifest by the leakage of the pipeline contents, the leaked material produces a characteristic trace or signal. Typically, failures in pipelines are currently determined by having personnel walk the pipeline on a periodic and costly basis with means to detect the trace or signal.

It is understood that pipelines usually carry petroleum, natural gas, refined petroleum or gas products, chemicals, mineral ore slurries and other fluid or fluidized substances or mixtures.

When electromagnetic radiation from either a natural or man-made source interacts with matter a number of phenomena may occur including scattering, absorption, transmission and reflection. When the interactions of electromagnetic radiation and matter are carefully examined, analyzed, and represented in an ordered fashion as a function of wavelength, frequency, or time this is referred to as a spectral or spectroscopic analysis. During spectroscopic analyses different materials exhibit different scattering, absorption, reflection and transmission characteristics. These characteristics are determined by the chemical and physical structure of the materials. When a set of these characteristics are determined to a given level of certainty, as with the use of known test subjects, these spectroscopic results may be referred to as reference spectral signatures or reference spectra. Natural gas characteristically contains a mixture of methane, ethane, and small amounts of other gases. Gas generated by the decomposition of organic matter henceforth referred to as swamp gas, only contains methane. It is highly desirable for a method of detection to be able to distinguish between gases released as a result of a failure in a pipeline or holding container versus swamp gases in this manner avoiding false alarms. It is possible to use methods involving illuminants and their corresponding interaction with the probed areas to detect the presence of various chemical compositions and mixtures as described by Windig in U.S. Pat. No. 5,481,476. This patent describes the chemometric analysis of data. This patent provides for a quantitative method of determining remotely the nature of chemicals detected by the probe. In many cases this provides the required certainty for avoiding false alarms and potentially the capability of identifying the source(s) of the detected species. This same methodology can be applied to species other than natural gas Electromagnetic radiation can be directed onto a test subject by any of a variety of means. Commonly lasers are used but other means such as the use of antennas for radio and microwave electromagnetic energy may be used. Hereafter when electromagnetic radiation is directed onto a test subject it is referred to as an illuminant.

Raman spectral signatures for natural gas components are well known. Hansen et. al., Appl. Spectrosc. 55(1), p. 55 (2001) have recently reported laboratory studies of natural gas samples at high pressure.

SUMMARY OF THE INVENTION

It is an object of the present invention to provide an improved way to automatically determine if there is a failure in a natural gas pipeline.

This object is achieved by a method for detecting failures in a natural gas pipeline comprising the steps of:
  (a) illuminating portions of the pipeline from a remote platform;
  (b) detecting returning radiation from the pipeline;
  (c) determining that there is a failure in the pipeline when the spectral signature indicates that there is a plume of escaping natural gas from the pipeline escaping from a failure; and
  (d) indicating to a customer that a failure in the pipeline has been detected at a predetermined coordinate position.

In many cases it is required to inspect natural gas pipelines frequently in order to determine the likelihood or development of failures since such failures can be catastrophic to the environment. In many cases these inspections are done by a ground site survey; individuals visit these locations and take measurements or other form of data on-sight. This process becomes cumbersome, costly, inconvenient, and in many cases unreliable and unsafe due to the dangers present in remote locations and to potential false interpretations due to worker fatigue and other factors. Furthermore, remote locations are frequently in mountains, deserts and forests that are difficult to reach and frequent inspection requires the placement of permanent maintenance and inspection crews adding to overall costs. It is an advantage of the present invention to provide a more effective way of determining failures in natural gas pipelines by automatically processing images captured from a remote platform. This automatic processing can include comparing with previously detected images. This automatic processing can also include algorithms and expert systems that act in a predictive manner.

A feature of the present invention is that an emission plume created by natural gas escaping from a pipeline whether on the surface or below interacts with laser light to provide a detectable spectral signature. This spectral signature is then used in accordance with the present invention to determine if there is a failure. Furthermore when natural gas is under pressure and it escapes, as in the case of a failure, from a pressurized container like pipeline or cylinder the natural gas undergoes thermal changes characteristic of the natural gas and based on the corresponding Joule-Thompson coefficient. These thermal changes can also be detected remotely in accordance with the present invention.

DESCRIPTION OF THE PREFERRED EMBODIMENTS

Figure 1:
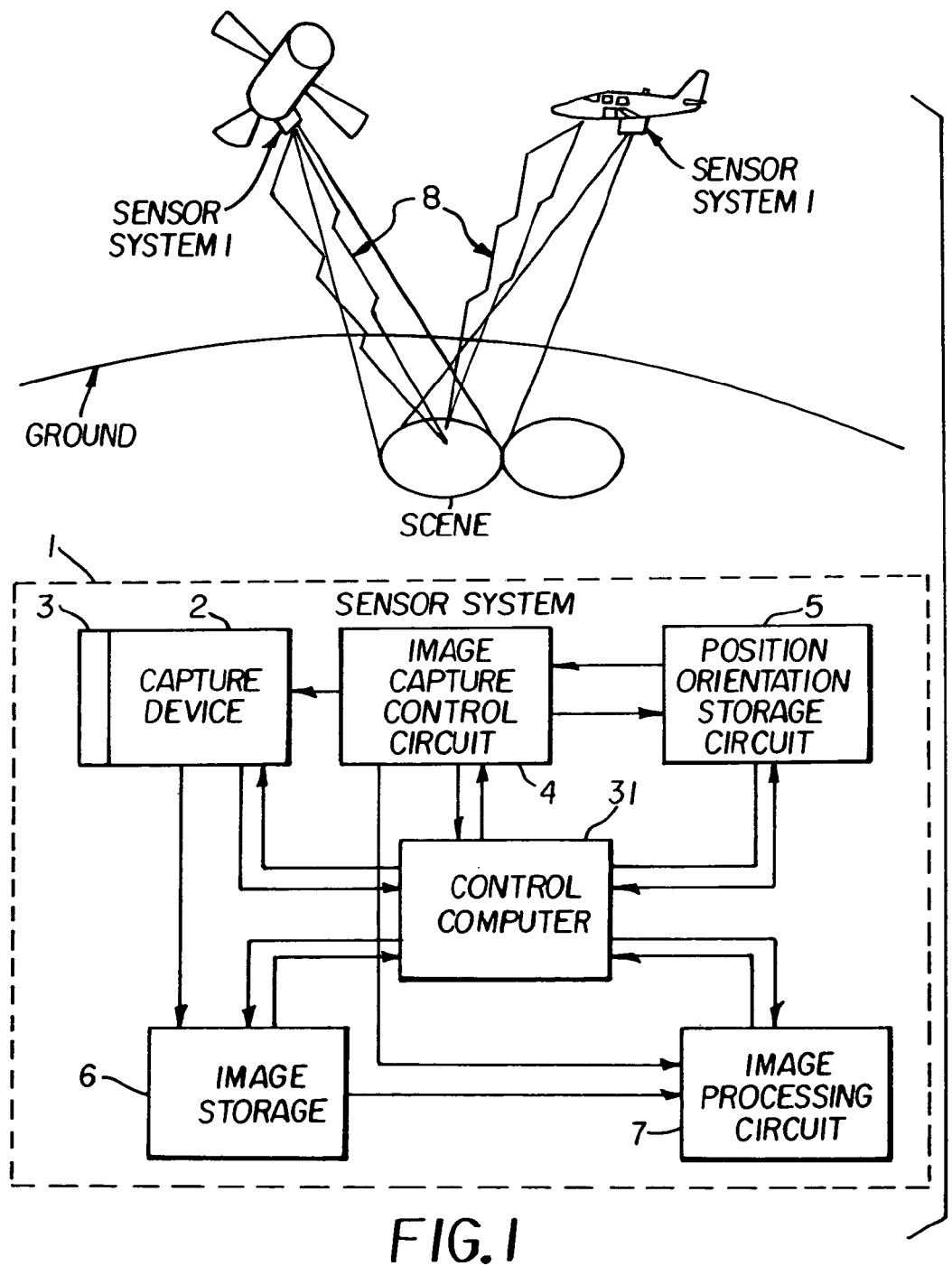
FIG. 1 depicts a system for capturing images from an airborne or a satellite platform in accordance with the present invention; it further includes an on-board illuminant system (e.g. laser)

A sensor system 1 is employed in the capturing of images in order to identify material failures in a natural gas pipeline. Images of the ground containing natural gas pipelines are captured by a remote platform by this sensor system 1. Sequential images may be captured in digital form and either stored in the remote platform (for example, an aerial or satellite platform) to be transferred later or transmitted via a radio link to a control ground station. The capture device 2 includes an electronic sensor, typically a, charge coupled device (CCD) or complementary metal oxide semiconductor (CMOS) imaging array that along with some imaging optics captures a sampling of the scene in electronic form. In some instances a non-imaging sensor such as a photomultiplier tube or photodiode may be employed to detect the light signal that originates from a portion of the scene. An image may be constructed by scanning the non-imaging sensor over portions of the scene. For example radar signals are detected in such a scanned mode and an image is constructed that represents the intensity of the received radar signal as a function of position in the scene. In some instances a special optical filter 3 is attached to the input to the CCD or CMOS detector to filter the light wavelengths that are incident upon the detector. This optical filter 3 is chosen so as to maximize the signal-to-noise ratio for the detection of a specific type of pipeline failure. Alternatively, the ground location image of a scene can be captured by conventional photographic cameras. Film images would then have to be converted to digital images by an image scanner that includes an image sensor. The sensor system 1 also has an image capture control circuit 4 that sequences the operation of the capture device 2. As will be clear from FIG. 1, the operation of the various elements shown in sensor system 1 is under the control of a control computer 31. The image capture control circuit 4 controls capture device 2 and sends position and orientation information to a position and orientation storage circuit 5 with each captured image. The customer provides spatial coordinate position information. This is done in order to identify the location of man-made structures of interest, in this case, a natural gas pipeline. Such position information is also stored in position and orientation storage circuit 5. Georeferencing technology is frequently used to establish the current position and orientation of the aerial platform. Such georeferencing technology includes the use of Global Positioning System receivers and the like. Position and orientation data are used along with predetermined coordinate positions to locate the man-made structures in the captured image. Control computer 31 causes image data to be stored in image storage 6 and can be processed to identify features of a scene in image processing circuit 7. The processing sequence is also directed by control computer 31 of the image data in this instance is to enhance the capability of the sensor system 1 to identify material failures in man-made structures. The image processing circuit 7 includes a storage memory (not shown) that includes a representation of different material failures to be detected and comparing the captured digital image with the material failures to determine the presence of a material failure, type of material failures and location of the material failures in natural gas pipelines. With the exception of the capture device 2, the various elements of the sensor system 1 may be located either in the remote platform or at the ground station location. Moreover, many of the elements described can be embodied in software that can be understood to be within the control computer 31. The capture device 2 is located in either the aerial or satellite platform or a fixed structure spaced above the ground. The remote platform may optionally contain an onboard illuminant 8. As already mentioned this onboard illuminant 8 may be a laser or microwave or other electromagnetic radiation source and some means to direct the radiation produced to the area of interest on or near the ground. The area of interest including the natural gas pipeline has been previously identified by the customer through the supplied customer coordinate data 9 (shown in FIG. 2).

Figure 2:
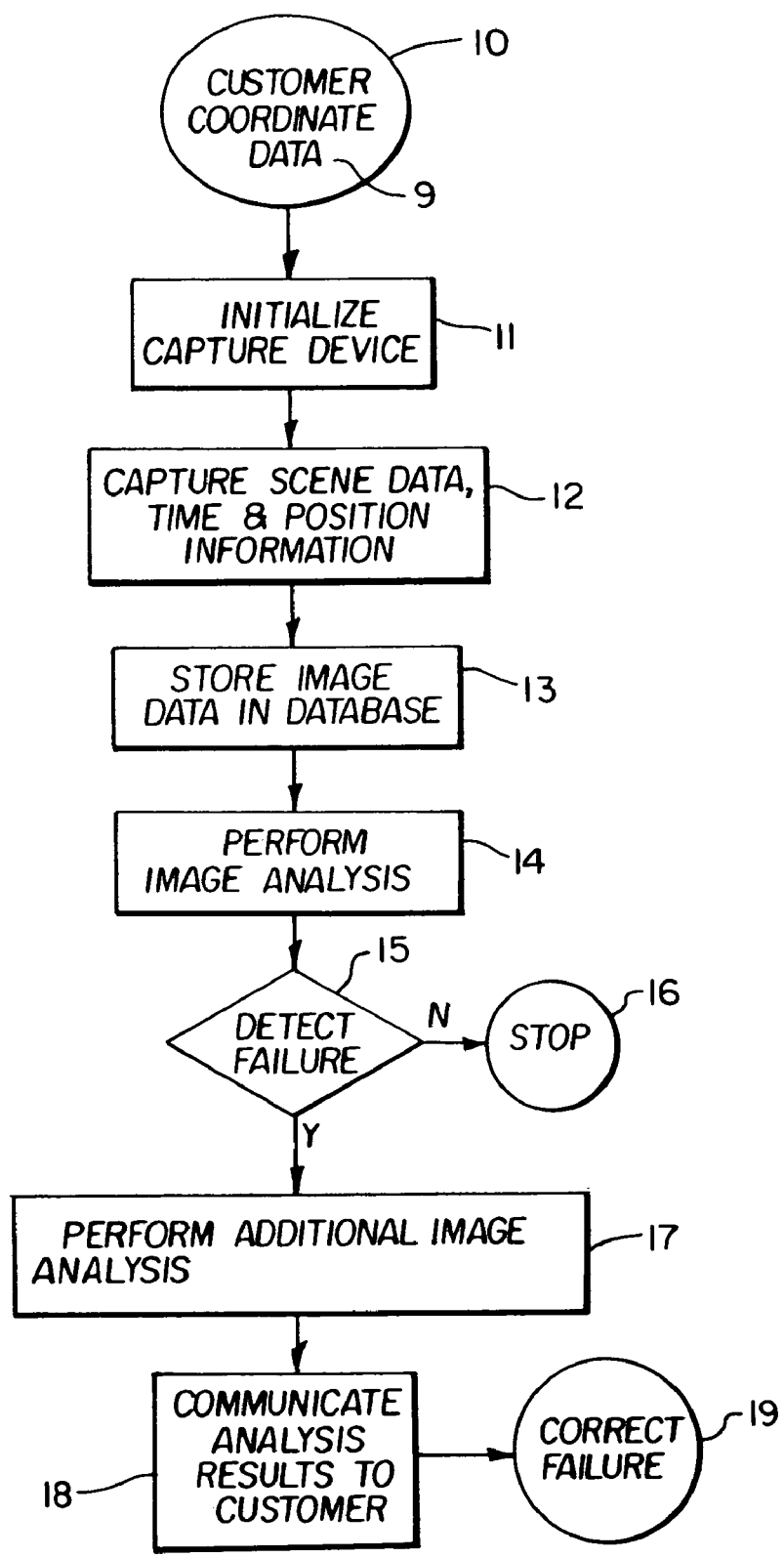
FIG. 2 is a flowchart in block diagram form of the process of interrogating the test subject (pipeline) capturing and processing images to detect pipeline failures and communicating with a customer.

The overall process for detecting material failures in pipelines is depicted in flowchart form in FIG. 2. The flowchart is in block diagram form and those skilled in the art will appreciate that many of the functions are controlled by the control computer 31. Once the customer's coordinate data 9 has been provided it is input to the sensor system 1 in input block 10, thus establishing the area of interest, the next event includes initializing the capture device 2 and image storage 6 to erase any previously captured scene data. This occurs in block 11. Next a new scene is captured in block 12 using the position information supplied by the customer to trigger recording of the images. The image data along with position and time information necessary to identify the location and time of the current scene is stored in order to facilitate comparison with the same scene taken at other times. Image and other data are stored in a scene database in block 13 in order to perform such comparisons at a future time. Image analysis is next performed in block 14 in order to identify changes in the scene and facilitate identification of failures in the natural gas pipeline that appear in the scene. The latest scene image is compared with image data that has been previously stored in the block 13. The process next requires a decision 15. If a natural gas pipeline failure is not detected the process stops at stop process action 16. Detection of a natural gas pipeline failure may initiate further image analysis in block 17 as required by a customer. The identification process finishes with the results of the analysis communicated to the customer in block 18. The communication makes take many forms, for example a telephone contact or e-mail notification of the detection of the natural gas pipeline failure. The final step in the process is to correct the natural gas pipeline failure performed in correct failure action 19.

Figure 3:
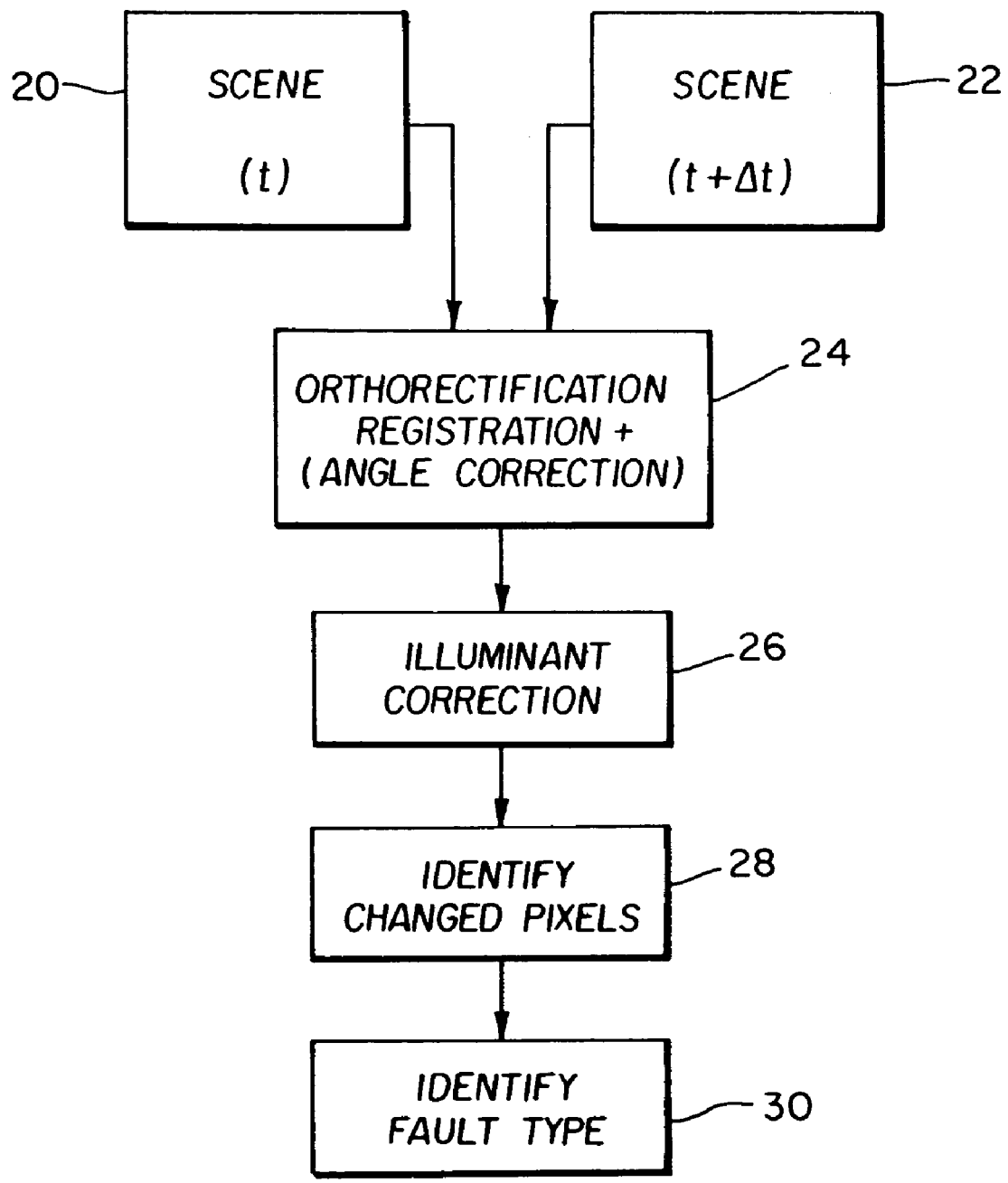
FIG. 3 is a flowchart in block diagram form of an image processing algorithm, which can be used in the system shown in FIG. 1.

FIG. 3 depicts the algorithm used to process image data files from a database and identifies natural gas pipeline failures. Two separate data files describing scene 20 and scene 22 are made available for comparison. Both data files contain the same scene content, but they typically record images taken at different times. That is, the time between capturing the two images differs by a time Δt. In block 24 image files or scenes undergo the process of orthorectification, that is, compensation for variations in position and angle at the time the scenes were recorded. The scenes are also registered at this point in the process. This process is performed in order to allow an exact pixel-by-pixel comparison of the elements of a scene or image. Block 26 describes the optional illumination correction step. It may or may not be necessary to correct the data in each scene for differences in the illumination at the time each scene was recorded. Onboard illuminant levels may be recorded at the time of image capture in order to facilitate precise comparison at a later time. Changes in the scene identified in block 28, are used by the control computer 31 by detecting, using software, differences in the pixel content of the two scenes to be compared. Such changes may be reflected in the intensity of the pixels, or in the shape of an object, corresponding to a finite collection of pixels. Such methods for identification of pixel or object changes are well known to those skilled in the art. On the basis of such pixel changes the natural gas pipeline failure type is identified in block 28.

Figure 4:
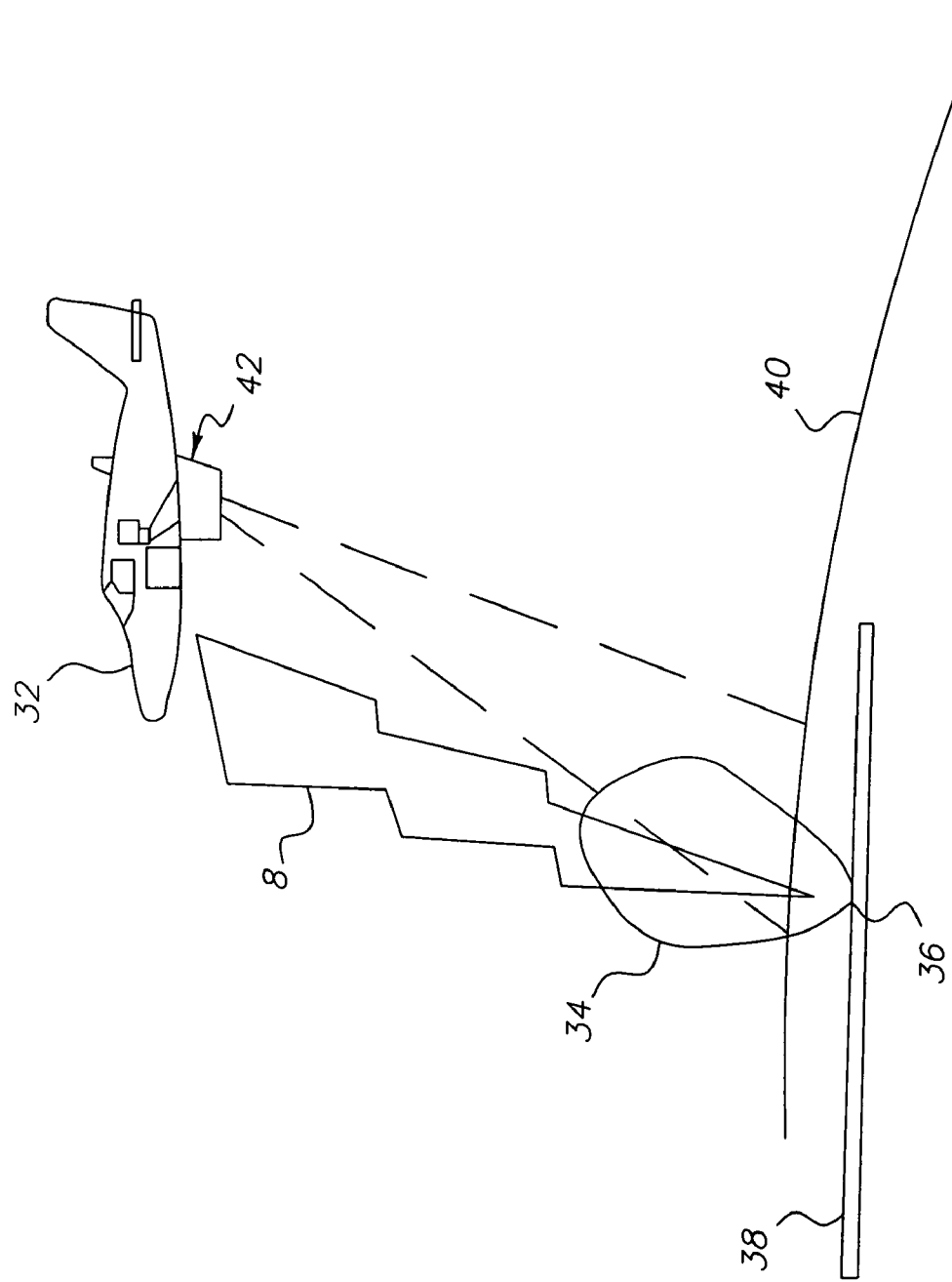
FIG. 4 depicts the remote examination of a leaking natural gas pipeline and detection of a plume of escaping natural gas.

FIG. 4 illustrates a somewhat different embodiment of the present invention. An aerial platform 32 is depicted with a sensor system 42 and an onboard illuminant 8. The onboard illuminant 8 is shown being directed at a natural gas plume 34 leaking from a failure 36 in a buried natural gas pipeline 38. The buried natural gas pipeline 38 is located beneath the surface of the ground 40. For example, the illuminant 8 may include a pulsed laser system directed at the natural gas plume 34. In this case the sensor system 42 is optimized to detect the returning radiation as backscattered Raman light from the natural gas plume 34, through the appropriate choice of optical filter 3 (described in FIG. 1). For Raman analyses it is appropriate to consider the use of spectrometers or spectrographs for use as the optical filter 3. Raman spectroscopy is based upon the inelastic scattering of light; chemical components scatter light at frequencies different from the exciting light frequency. The differences are indicative of the various energy levels of the molecular or chemical components. The preferred embodiment of the detection system includes an optical system optimized to detect the vibrations of methane (at 2920 $cm^{-1}$) and ethane (at either 2957 or 996 $cm^{-1}$). Natural gas samples typically consist of approximately 85% methane and smaller concentrations (~10–15%) of ethane. As discussed previously, ethane is found in natural gas, but not swamp gas samples. Hence the presence of spectral features unique to ethane, e.g. the 2957 $cm^{-1}$ band, concurrent with the presence of the strong 2920 $cm^{-1}$ methane Raman band is strongly indicative of a natural gas leak at a position identified as proximate to a natural gas pipeline, buried or otherwise. Alternatively, the sensor system may sense infrared returning radiation at wavelengths appropriate for the detection of ethane and methane. For ethane the absorption band at ~2977 $cm^{-1}$ is typically used, while for methane there is an absorption at ~3044 $cm^{-1}$. In this manner the presence of the leaking hydrocarbon natural gas is directly detected.

In a different embodiment of this invention, the natural gas plume can be detected through the temperature difference a leaking, high pressure gas produces. It is well known to those skilled in the art that rapidly expanding gases are cooled by virtue of the Joule-Thompson effect. A natural gas plume, because of the pressure difference inside and outside of the pipeline, is necessarily at a lower temperature than gas inside the pipeline. This can cause sufficient temperature contrast to make the natural gas plume detectable by thermal radiation imaging means. The observation of a temperature difference in the predetermined coordinate position of a natural gas pipeline would constitute a thermal radiation signature of a natural gas pipeline failure.

Figure 5:
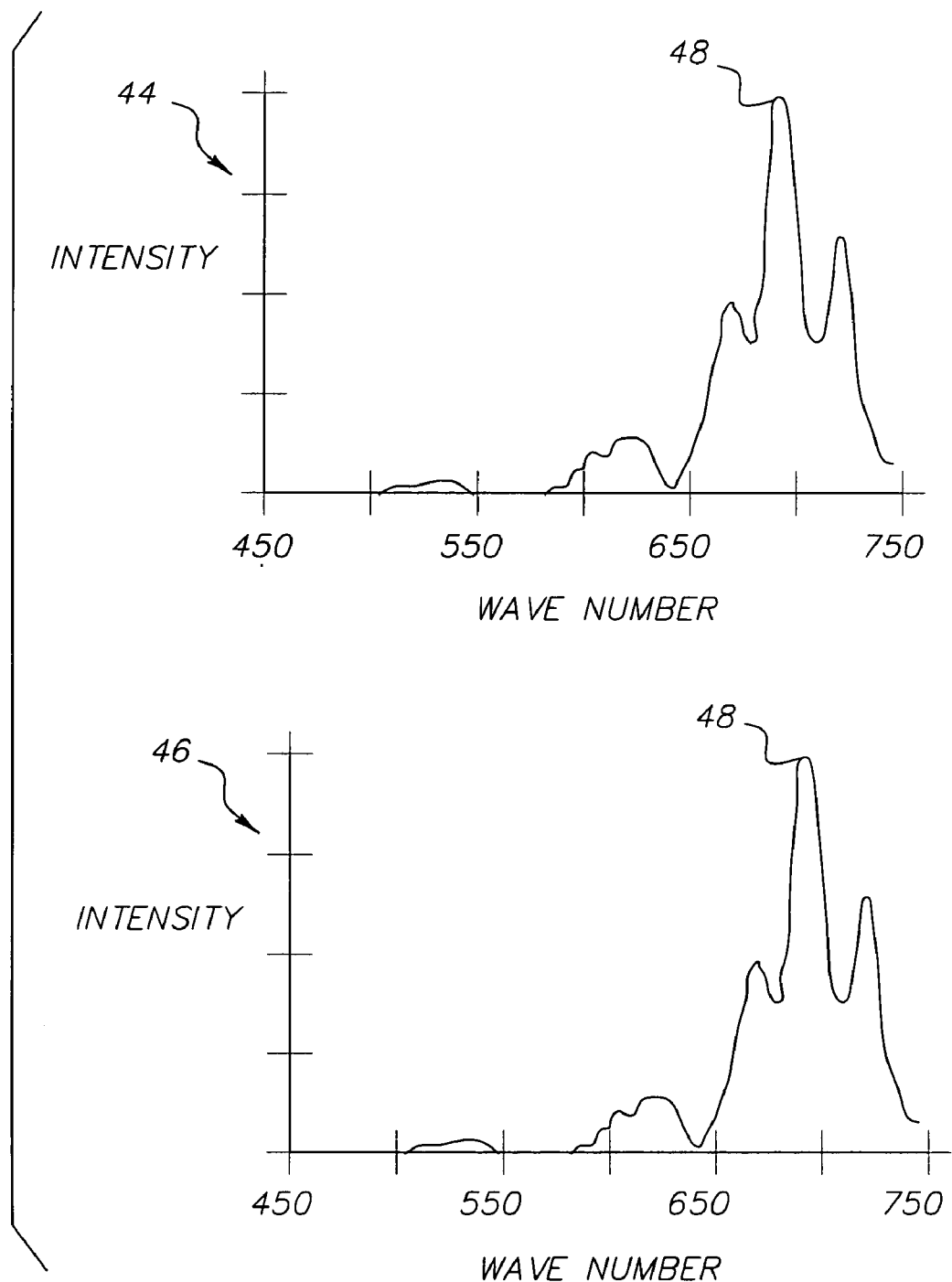
FIG. 5 depicts both a reference spectral signature and a spectral signature and their comparison.

FIG. 5 depicts both a reference spectral signature 44 and a spectral signature 46 and their comparison, and illustrates the method of analysis to determine mixture composition. As noted previously the interactions of electromagnetic radiation and matter are carefully examined, analyzed, and represented in an ordered fashion as a function of wavelength, frequency, or time and this is referred to as a spectral or spectroscopic analysis. During spectroscopic analyses different materials exhibit different scattering, absorption, reflection or transmission characteristics. These characteristics are determined by the chemical and physical structure of the materials. When a set of these characteristics are determined to a given level of certainty, as with the use of known test subjects, these spectroscopic results may be referred to as reference spectral signatures 44 or reference spectra. The spectral signature 46 of a test subject is the spectrum of an unknown, in this case, a section of natural gas that is being evaluated for a failure. FIG. 5 depicts both the reference spectral signature 46 and a spectral signature 46 of a test subject and thus facilitates their comparison. Those skilled in the spectroscopic art would perform such a comparison by attempting to identify characteristic spectral peaks 48 in both spectra in order to identify a match condition. In FIG. 5., such a match is readily accomplished. Typically, reference spectral signatures 44 are obtained under somewhat idealized laboratory conditions, whereas the spectral signature 46 of the test subject is compromised due to additional noise sources, contaminants, etc. In these circumstances the apparatus described by Windig in U.S. Pat. No. 5,481,476 provides additional capability for the spectral analysis of complex mixtures. This patent describes the chemometric analysis of data.

Figure 6:
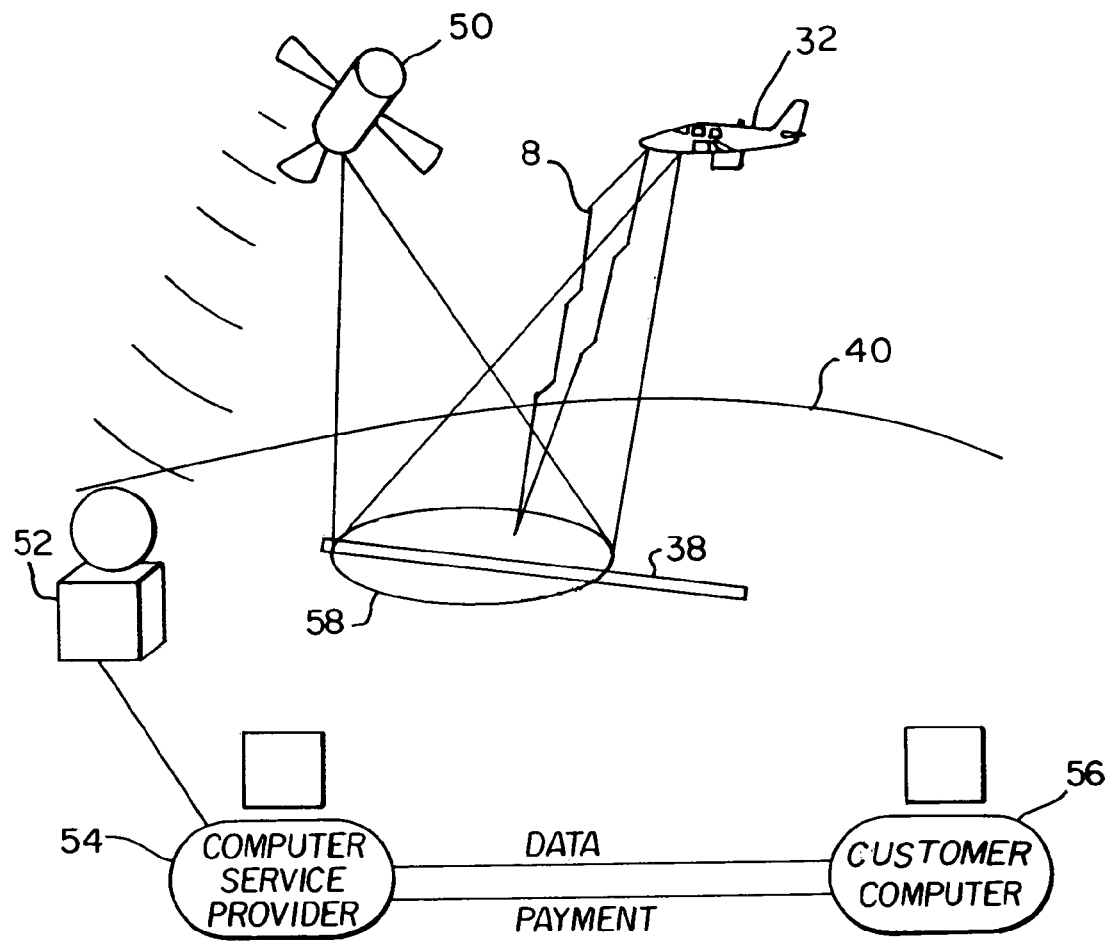
FIG. 6 illustrates the capturing of an image, analysis to identify a pipeline failure, and communication over a channel to deliver information to and receive payment from a customer.

FIG. 6 illustrates the capturing of an image, analysis to identify a natural gas pipeline failure and communication over a computer network to deliver information to and receive payment from the customer. A satellite 50 or an aerial platform 32 captures an image of a scene 58 that contains a natural gas pipeline 38 to be analyzed. The image data is transmitted to a ground station 52 and transferred to the service provider's computer system 54. The image data is analyzed as previously described to determine whether a natural gas pipeline failure has occurred. If a failure or fault is detected the customer for the service receives notification of the failure. This notification occurs via a channel for example, a computer network such as the Internet, or via other means, such as telephony. The customer computer 56 receives the notification directly from over the computer network. The customer subscribes to the service and pays for the service via the computer network. In this manner, the timely delivery of information regarding the status of a failure can be transmitted to the customer and the quality of service can be assured to be at a sufficiently high level.

The invention has been described in detail with particular reference to certain preferred embodiments thereof, but it will be understood that variations and modifications can be effected within the spirit and scope of the invention. For example, the control computer 31 can itself be reprogrammed from a remote location and would include all the necessary communication links to permit such reprogramming.

PARTS LIST 1 sensor system
2 capture device
3 optical filter
4 capture control circuit
5 position and orientation control circuit
6 image storage
7 image processing circuit
8 onboard illuminant
9 customer coordinate data
10 input block
11 block
12 block
13 block
14 block
15 decision
16 stop process action
17 block
18 block
19 correct failure action
20 scene
22 scene
24 orthorectification block
26 illumination correction block
28 identification block
30 identify pipeline failure block
31 control computer
32 aerial platform
34 natural gas plume
36 failure Parts List Cont'd.
38 natural gas pipeline
40 ground
42 sensor system
44 reference spectral signature
46 spectral signature
48 spectral peaks
50 satellite
52 ground station
54 service provider's computer system
56 customer computer
58 scene

What is claimed is:

1. A method for detecting failures in a natural gas pipeline comprising the steps of:
   (a) illuminating portions of the natural gas pipeline from a remote platform;
   (b) nearly simultaneously detecting Raman spectral signatures indicating a concentration of about 85% methane and 10–15% of ethane escaping from the natural gas pipeline;
   (c) determining that there is a failure in the natural gas pipeline when the Raman spectral signatures indicate that there is a plume of escaping natural gas from the pipeline; and
   (d) indicating to a customer that a failure in the natural gas pipeline has been detected at a predetermined coordinate position.

2. The method claimed in claim 1, wherein the Raman spectral signatures are obtained by analysis of backscattered Raman light.

3. A system for remote natural gas detection from a pipeline, comprising:
   a) a remote platform;
   b) a source of illuminant on the remote platform;
   c) a capture device for receiving returning radiation that indicates presence of both methane and ethane in a concentration of about 85% methane combined with a concentration of 10–15% of ethane, such that a natural gas plume is identifiable in an image;
   d) means for analyzing spectral signatures of both methane and ethane, wherein the spectral signatures are Raman spectral signatures;
   e) an image storage device for storing the image;
   f) an image processor for analysis of the returning radiation;
   g) means for position and orientation control of the remote platform; and
   h) means for controlling the system.

4. The system claimed in claim 3, wherein the source of illuminant is predetermined for a specific wavelength according to a spectral signature of the presence of both methane and ethane.

5. The system claimed in claim 4, wherein the spectral signature is obtained by analysis of backscattered Raman light.

6. The system claimed in claim 4, wherein the spectral signature indicates a concentration of about 85% a methane and 10–15% of ethane.

7. The system claimed in claim 3, wherein the remote platform is located on an aerial or satellite platform.

8. The system claimed in claim 3, wherein the means for position and orientation control is a global positioning system.

9. The system claimed in claim 3, wherein the capture device includes an electronic sensor selected from the group consisting of charge coupled device (CCD), complementary metal oxide semiconductor (CMOS), photomultiplier tube, and photodiode.

10. The system claimed in claim 3, wherein the source of illuminant is a laser.

11. The system of claim 3 further including means for determining a location of the failure relative to a position of the aircraft using georeferencing technology.

12. The system of claim 3 further including an imager for capturing one or more images of an area where there are identifiable failures, from the remote platform, using predetermined coordinates of the natural gas pipeline.

13. The system of claim 3 further including means of correcting a failure in the natural gas pipeline based on the analysis by the image processor.

14. The system of claim 13 further including means of billing a customer a charge after the failure has been detected.

* * * * *